United States Patent [19]

Minderhoud et al.

[11] Patent Number: 4,579,985

[45] Date of Patent: Apr. 1, 1986

[54] PROCESS FOR THE PREPARATION OF HYDROCARBONS

[75] Inventors: Johannes K. Minderhoud; Swan T. Sie; Ernst J. R. Sudhölter, all of Amsterdam, Netherlands

[73] Assignee: Shell Oil Company, Houston, Tex.

[21] Appl. No.: 669,406

[22] Filed: Nov. 8, 1984

[30] Foreign Application Priority Data

Nov. 15, 1983 [NL] Netherlands ............ 8303909

[51] Int. Cl.[4] .............................................. C07C 1/04
[52] U.S. Cl. ................................. 585/310; 208/110; 208/950; 518/704; 518/715; 585/319; 585/324; 585/469; 585/638; 585/653
[58] Field of Search ............ 208/108, 110, 112, 950; 518/704, 715; 585/319, 324, 310, 469, 638, 648, 653

[56] References Cited

U.S. PATENT DOCUMENTS

| | | | |
|---|---|---|---|
| 2,467,966 | 4/1949 | Clark | 518/715 |
| 4,385,193 | 5/1983 | Bijwaard et al. | 585/310 |
| 4,410,637 | 10/1983 | Korbeck et al. | 518/714 |
| 4,499,209 | 2/1985 | Hoek et al. | 585/310 |
| 4,522,939 | 6/1985 | Minderhoud et al. | 502/242 |

OTHER PUBLICATIONS

Kirk-Othmer, Encyclopedia of Chemical Technology, vol. 11, 3rd Ed., 1980 (John-Wiley) pp. 473-478.

*Primary Examiner*—John Doll
*Assistant Examiner*—A. Pal
*Attorney, Agent, or Firm*—Kimbley L. Muller

[57] ABSTRACT

$C_5^+$ hydrocarbons are prepared from $C_4^-$ hydrocarbons by a two-stage process comprising steam reforming followed by Fischer-Tropsch synthesis over a special cobalt-containing catalyst; a gaseous fraction comprising unconverted $H_2$ and CO as well as $C_4^-$ hydrocarbons and $CO_2$ formed as by-products is separated from the synthesized product and recycled to the steam reformer.

16 Claims, No Drawings

PROCESS FOR THE PREPARATION OF HYDROCARBONS

BACKGROUND OF THE INVENTION

The invention relates to a process for the preparation of hydrocarbons having at least five carbon atoms per molecule.

Hydrocarbons of at least five carbon atoms per molecule (hereinafter referred to as "$C_5+$ hydrocarbons") can be prepared from hydrocarbons having at most four carbon atoms per molecule (hereinafter referred to as "$C_4-$ hydrocarbons") by a two-step process in which in the first step the $C_4-$ hydrocarbons are converted by steam reforming into a mixture of carbon monoxide and hydrogen, which mixture is contacted in the second step at elevated temperature and pressure with a catalyst and thus converted into a mixture of hydrocarbons consisting substantially of $C_5+$ hydrocarbons. The reaction which takes place in the second step of the process is known in the literature as the Fischer-Tropsch hydrocarbon synthesis. Catalysts often used for this reaction contain one or more metals from the iron group together with one or more promoters and a carrier material.

A catalyst's usefulness for the preparation of $C_5+$ hydrocarbons from $H_2/CO$ mixtures is mainly determined by the catalyst's activity, $C_5+$ selectivity and stability, the catalyst being regarded as more useful according as these parameters have a higher value. In the preparation of $C_5+$ hydrocarbons from $C_4-$ hydrocarbons according to the above-mentioned two-step process the catalyst's stability draws most emphasis. For according as the catalyst has a higher stability, the process can be carried out for a longer period before it becomes necessary to replace the catalyst. It is true that, according as the catalyst has a lower activity, less of the $H_2/CO$ mixture will be converted per reactor throughput, and more $C_4-$ hydrocarbons will be formed as by-product according as the catalyst has a lower $C_5+$ selectivity, but by recycling unconverted $H_2$ and $CO$ and also by recycling the $C_4-$ hydrocarbons formed as by-product a high conversion of the $H_2/CO$ mixture and a high $C_5+$ selectivity can be realized all the same. Thanks to the possibilities of compensating for lower activity and $C_5+$ selectivity offered by the two-step process, for carrying out the process on a technical scale preference will often be given to a catalyst for the second step which, though not having the highest activity and $C_5+$ selectivity, is the most stable.

Since the steam reformation of $C_4-$ hydrocarbons leads to the formation of a $H_2/CO$ mixture having a $H_2/CO$ molar ratio higher than 2, whilst Fischer-Tropsch catalysts have a $H_2/CO$ consumption ratio of at most about 2, the excess hydrogen formed during the process will have to be removed in order to prevent $H_2$ build-up in the system when the two-step process is carried out with use of recycle. Besides, when carrying out the two-step process using recycle, the part of the steam added during the steam reforming which has remained unconverted, as well as steam formed as by-product in the second step, should also be removed during the process. The quantity of hydrogen to be removed is dependent on the H/C atomic ratio of the feed for the first step, the CO-shift activity of the catalyst used in the second step and the degree of $CO_2$ formation during the steam reforming. On the assumption of a stoichiometric conversion of the feed during the steam reforming according to the equation $C_nH_{2n+2}+nH_2O \rightarrow nCO+(2n+1)H_2$, the synthesis gas obtained will have a higher $H_2/CO$ molar ratio according as the feed for the first step has a higher H/C atomic ratio, and therefore more hydrogen will have to be removed during the process. For instance, starting from methane (having $n=1$) as feed for the steam reforming, a synthesis gas can be obtained by the reaction given above which has a $H_2/CO$ molar ratio of $(2n+1)/n=3$. According as the catalyst used in the second step has higher CO-shift activity, a larger part of the amount of CO present in the synthesis gas will react with the water formed as by-product in the hydrocarbon synthesis according to the equation $CO+H_2O \rightarrow CO_2+H_2$, leading to an increase of the $H_2/CO$ molar ratio, and therefore more hydrogen will have to be removed in the process. As regards the formation of carbon dioxide during the steam reforming, the following may be observed. As described hereinbefore, when the steam reforming reaction proceeds stoichiometrically, there will be formed from each g atom C present in the feed, one g mol CO. However, in actual practice it is seen that depending on the conditions under which the steam reforming is carried out, part of the carbon present in the feed is converted into carbon dioxide. On account of this side reaction the synthesis gas obtained has a $H_2/CO$ molar ratio which is higher than at a stoichiometric development of the steam reforming. In the process more hydrogen will therefore have to be removed according as more carbon dioxide is formed in the steam reforming.

In order to keep the amount of hydrogen to be removed as small as possible when carrying out the two-step process with use of recycle starting from a feed with a given H/C atomic ratio, preference is given in the first place to the use in the second step of a catalyst with the highest possible $H_2/CO$ consumption ratio. It is also preferred to add carbon dioxide to the feed for the first step in order to suppress carbon dioxide formation during the steam reforming. With a view to optimum utilization of the carbon present in the feed for the formation of carbon monoxide, it is preferred to use carbon dioxide present in the reaction product of the first step for this purpose. This product can be scrubbed to separate the carbon dioxide, which can be recycled to the steam reforming. This procedure is attended with serious drawbacks. Apart from the fact that the removal of carbon dioxide from a gas stream by the use of scrubbing, in which often an amine-solution is used from which the carbon dioxide must be separated afterwards, is a rather costly process when carried out on a technical scale, it is a consequence of this mode of carbon dioxide removal that the carbon dioxide which originally was at the pressure level required in the process, is at an atmospheric pressure after separation and has to be re-pressurized to the pressure level of the process before it can be introduced into the steam reforming.

It would of course be much more attractive if it were possible to keep the carbon dioxide formed in the reaction product and not to separate it until after the second step. By dividing the reaction product of the second step into a liquid fraction substantially consisting of $C_5+$ hydrocarbons and water and a gaseous fraction substantially consisting of unconverted hydrogen and carbon monoxide, $C_4-$ hydrocarbons and carbon dioxide, and recycling the gaseous fraction to the steam reforming, there could be created a carbon dioxide recycle without there being the need to depressurize and then again to pressurize the carbon dioxide. However, the use of such a process on a technical scale is to a great extent dependent on the influence which carbon dioxide has on the catalyst in the second step. As stated hereinbefore, in the two-step process with use of recycle stability is a parameter of particular importance; however, this does not imply that any negative influence which carbon dioxide may have on the activity or $C_5+$ selectivity is regarded unimportant.

In order to get a fair knowledge of the influence of carbon dioxide on the performance of Fischer-Tropsch catalysts, an investigation was carried out in which these catalysts were used for the conversion of gas mixtures some containing carbon dioxide in addition to $H_2$ and CO, some not. It was found that the presence of carbon dioxide in the $H_2$/CO mixture lessens the activity of these catalysts, the decrease becoming larger as the mixture contained more carbon dioxide. It is true that by increasing the severity of the reaction conditions—notably raising the temperature and/or pressure—in the presence of carbon dioxide an activity level could be attained which corresponded with that of a carbon dioxide-free operation, but this was attended with a loss of the catalysts' stability, which became larger as severer reaction conditions were used. It was further found that the $C_5+$ selectivity of these catalysts was barely influenced by the presence of carbon dioxide in the $H_2$/CO mixture. As regards the stability the investigation yielded a surprising finding. In contrast with other Fischer-Tropsch catalysts whose stability—as well as $C_5+$ selectivity—was barely influenced by the presence of carbon dioxide, there was a certain group of cobalt catalysts whose stability was found to be considerably increased by the presence of carbon dioxide, the increase being larger according as the mixture contained more carbon dioxide. The Fischer-Tropsch catalysts displaying this surprising behavior comprise silica, alumina or silica-alumina as carrier material and cobalt together with zirconium, titanium and/or chromium as catalytically active metals in such quantities that in the catalysts there are present 3–60 pbw cobalt and 0.1–100 pbw zirconium, titanium and/or chromium per 100 pbw carrier material. The catalysts are prepared by depositing the metals concerned by kneading and/or impregnation on the carrier material. For further information on the preparation of these catalysts by kneading and/or impregnation reference is made to U.S. patent application Ser. No. 594,618 filed on Mar. 29, 1984, which is incorporated herein by reference.

When a cobalt catalyst belonging to the afore-mentioned class is used for the conversion of a $H_2$/CO mixture containing no carbon dioxide, this catalyst is seen under the given reaction conditions to have not only high stability and $C_5+$ selectivity, but also very high activity. When the same catalyst is used under similar reaction conditions for the conversion of a gas mixture which, in addition to $H_2$ and CO, contains carbon dioxide, a decrease in activity is seen, as was remarked hereinbefore. The decrease is smaller, by the way, than the decrease observed for other Fischer-Tropsch catalysts when the same amount of carbon dioxide is added to the gas mixture to be converted. However, in addition to the decrease in activity the cobalt catalysts show a considerable increase in stability. In view of the very high activity level of the present cobalt catalysts some loss of activity in return for a considerable increase in stability is quite acceptable for an operation carried out on a technical scale. Another option is to raise the activity to its original level by increasing the severity of the reaction conditions; this is coupled with some loss of stability. However, it has surprisingly been found that this loss of stability is amply compensated for by the increase in stability due to the presence of carbon dioxide. This means that when the cobalt catalysts belonging to the above-mentioned class are used for converting a carbon dixoide containing $H_2$/CO mixture, a degree of activity can be realized which is very similar to that seen in the carbon dioxide free operation, whilst the stability is higher. These special properties combined with a very high $H_2$/CO consumption ratio of about 2 render the cobalt catalysts eminently suitable for use in the second step of said two-step process carried out with use of recycle.

SUMMARY OF THE INVENTION

The present patent application therefore relates to a process for the preparation of $C_5+$ hydrocarbon from $C_4-$ hydrocarbson, in which in the first step $C_4-$ hydrocarbons are converted by steam reforming into a mixture of carbon monoxide and hydogen, which mixture is subsequently converted in a second step into a mixture of hydrocarbons consisting substantially of $C_5+$ hydrocarbons by contacting it at elevated temperature and pressure with a catalyst comprising 3–60 pbw cobalt and 0.1–100 pbw of at least one other metal chosen from the group formed by zirconium, titanium and chromium per 100 pbw silica, alumina or silica-alumina, which catalyst has been prepared by kneading and/or impregnation, in which the reaction product of the second step is divided into a gaseous fraction substantially consisting of unconverted hydrogen and carbon monoxide, $C_4-$ hydrocarbons formed as by-product and carbon dioxide formed as by-product, and a liquid fraction substantially consisting of $C_5+$ hydrocarbons and water at least part of which was formed as by-product in the second step, in which the gaseous fraction is recycled to the first step and in which the excess hydrogen formed and also the part of the water added during the steam reforming which has remained unconverted are separated off during the process.

DETAILED DESCRIPTION

In the process according to the invention the starting material is a feed consisting substantially of one or more $C_4-$ hydrocarbons. Examples of $C_4-$ hydrocarbons which may occur in the feed individually or in admixture are methane, ethane, propane, butane and isobutane. Preference is given to carrying out the process with a feed in which the $C_4-$ hydrocarbons consist mainly of methane. Special preference is given to natural gas a feed.

In the process according to the invention in the first step steam reforming is used to convert the $C_4-$ hydrocarbons into a mixture of carbon monoxide and hydrogen. The steam reforming is usually carried out by contacting the hydrocarbons to be converted together with steam at a temperature of 500°–1200° C., a pressure of 2–40 bar and a steam/hydrocarbon ratio of 1–10 g mol $H_2O$/g atom C with a catalyst comprising one or more metals from the iron group supported on a carrier. The steam reforming is preferably carried out at a temperature of 700°–1000° C., a pressure of 2–25 bar and a steam/hydrocarbon ratio of 1.5–5 g mol $H_2O$/g atom C and by using a nickel-containing catalyst. In order to prevent deposition of coke on the catalyst and also to remove coke already deposited from the catalyst by conversion into CO, it is preferred to use a catalyst containing an alkali metal, in particular potassium. Moreover, in order to avoid sintering of a catalyst, it is preferred to use a catalyst containing an alkaline earth metal, in particular calcium. If the $C_4^-$ hydrocarbons in the feed consist completely or to a considerable extent of hydrocarbons containing two or more carbon atoms per molecule, if it preferred to use a catalyst having cracking activity. The catalyst can be invested with cracking activity by the use of a silica-alumina as carrier material.

Steam which in the process according to the invention is to be separated from the reaction product has landed therein mainly in two different ways. In the first place steam finds its way into the reaction product because the steam reforming reaction is not a complete reaction, so that even when a stoichiometric quantity of steam is used, a minor portion of the amount used will be found in the reaction product in its original form. Usually the steam reforming is carried out by using excess steam. In that case not only the minor quantity mentioned before, but also the excess quantity used will appear in the reaction product. In the second place steam finds its way into the reaction product because it is formed as by-product in the hydrocarbon synthesis in the second step, according to the equation:

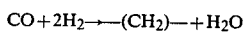

$$CO + 2H_2 \rightarrow (CH_2) - + H_2O$$

The carbon dioxide which in the process according to the invention is recycled to the first step has been formed substantially as by-product in the first step. In addition minor quantities of carbon dioxide may find their way into the reaction product by the occurrence of a side reaction in the second step.

The $C_4^-$ hydrocarbons which in the process according to the invention are recycled to the first step have been formed substantially as by-products in the second step. In addition minor quantities of $C_4^-$ hydrocarbons may find their way into the reaction product because a minor portion of the $C_4^-$ hydrocarbons used as feed remains unconverted or is only cracked to form $C_4^-$ hydrocarbons with a smaller number of carbon atoms.

In the process of the invention it is preferred to use in the second step the cobalt catalyst which form the subject matter of U.S. patent application Ser. No. 594,618 issued as U.S. Pat. No. 4,522,939 on June 11, 1985. These are catalysts which satisfy the relation $$(3+4R) > L/S > (0.3+0.4R),$$

wherein

L = the total quantity of cobalt present on the catalyst, expressed as mg Co/ml catalyst,
S = the surface area of the catalyst, expressed as $m^2$/ml catalyst, and
R = the weight ratio of the quantity of cobalt deposited on the catalyst by kneading to the total quantity of cobalt present on the catalyst.

The preparation of the cobalt catalysts which are used in the second step of the process of the invention is preferably carried out according to one of the three procedures mentioned hereinafter:

(a) first cobalt is deposited in one or more steps by impregnation and subsequently the other metal is deposited in one or more steps, also by impregnation, (b) first the other metal is deposited in one or more steps by impregnation and subsequently the cobalt is deposited in one or more steps, also by impregnation, and (c) first cobalt is deposited in one or more steps by kneading and subsequently the other metal is deposited in one or more steps by impregnation.

In the process according to the invention preference is given to the use in the second step of cobalt catalysts containing 15-50 pbw cobalt per 100 pbw carrier. The preferred quantity of other metal present in the cobalt catalysts depends on the way in which this metal has been deposited. In the case of catalysts where first cobalt has been deposited on the carrier, followed by the other metal, preference is given to catalysts containing 0.1-5 pbw other metal per 100 pbw carrier. In the case of catalysts where first the other metal has been deposited on the carrier, followed by the cobalt, preference is given to catalysts containing 5-40 pbw of the other metal per 100 pbw carrier. Preference is given to zirconium as other metal and to silica as carrier material. In order to be suitable for use the cobalt catalysts should first be reduced. This reduction may suitably be carried out by contacting the catalyst at a temperature between 200° and 350° C. with a hydrogen-containing gas.

In the process of the invention the second step is preferably carried out at a temperature of 125°-350° C. and a pressure of 5-100 bar. Special preference is given to a temperature of 175°-275° C. and a pressure of 10-75 bar for the second step.

In the process according to the invention steam should be removed from the reaction product. This can be done in a simple way by cooling the reaction product, so that the steam condenses. As stated hereinbefore, the reaction product contains both steam from the first step and steam from the second step. Steam can be separated from the reaction product at various stages. Steam from the first step can be separated after the first step and subsequently the steam from the second step can be separated after the second step together with the $C_5^+$ hydrocarbons. Another option is to separate the steam from the first step after the second step, together with the steam from the second step and the $C_5^+$ hydrocarbons.

In the process according to the invention the excess hydrogen formed should be removed from the reaction product. For the removal of hydrogen from the reaction product the known techniques for removing hydrogen from gas mixtures are eligible. For instance, in the present process the removal of part of the hydrogen from the reaction product can very suitably be carried out by using what is called pressure swing adsorption. This involves contacting the gas mixture from which hydrogen is to be removed under pressure with a solid adsorbents, such as a molecular sieve, active carbon or a mixture thereof, leading to selective adsorption of the components present in the gas mixture beside hydrogen. The components adsorbed from the gas mixture by the adsorbents can be desorbed by reduction of pressure and re-pressurized to the original pressure level by compression. In the present process the removal of part of the hydrogen from the reaction product by using pressure swing adsorption can very suitably be realized by applying this technique to a partial stream of the reaction product and, after hydrogen removal and compression, feeding this partial stream back into the head stream.

In the present process the removal of part of the hydrogen can also very suitably be carried out by membrane separation. To this end the reaction production is passed along a membrane, often consisting substantially of a polymer material which has the property of being more permeable to hydrogen than to the other components of the reaction mixture. If desired, the reduction of the hydrogen content of the reaction product by using membrane separation can be carried out in more than one step. Separation from the reaction product of the excess hydrogen formed can be carried out at various stages. Since at the present state of the art the removal of hydrogen from gas mixtures by using membrane separation or pressure swing adsorption is still problematic when the gas mixtures concerned contain steam, it is preferred in the present process to remove the hyrogen after the steam separation. If the steam separation is conducted after the first step and in addition after the second step, the hydrogen separation can be carried out optionally after the condenser following the first step or after the gas/liquid separator following the second step. If the steam separation is carried out exclusively after the second step, it will be preferred to carry out the hydrogen separation after the gas/liquid separator following the second step.

The cobalt catalysts used in the second step, in addition to the afore-mentioned surprising increase in stability in the presence of carbon dioxide, display the special property of yielding a product which contains only very minor quantities of olefins and oxygen-containing organic compounds and whose organic part is constituted virtually completely of unbranched paraffins, a considerable percentage of which boils above the middle distillate range. In this patent application middle distillates are taken to be hydrocarbon mixtures whose boiling range corresponds substantially with that of the kerosene and gas oil fractions obtained in the conventional atmospheric distillation of crude mineral oil. The middle distillate range lies substantially between about 150° and 360° C., the fractions boiling between about 200° and 360° C. usually being referred to as gas oils. On account of the high normal paraffins/isoparaffins ratio and the low content of olefins and oxygen-containing organic compound of the product prepared over the cobalt catalysts, the gas oil present therein has a very high cetane number.

It has been found that by hydrocracking in the presence of a catalyst containing or more noble metals of Groups VIII supported on a carrier the high-boiling part of said product can be converted in high yield into middle distillate. As feed for the hydrocracking at least the part of the product is choosen whose initial boiling point lies above the final boiling point of the heaviest middle distillate desired as end product. The hydrocracking, which is characterized by a very low hydrogen consumption, yields a product in which, owing to the high normal paraffins/isoparaffins ratio, the gas oil has a very high cetane number. Although in the preparation of middle distillates from the product obtained over the cobalt catalyst the part of the product whose initial boiling point lies above the final boiling point of the heaviest middle distillate desired as end product will do as feed for the hydrocracking, it is preferred to use for this purpose the total $C_5^+$ fraction of the product prepared over the cobalt catalyst, since it has been found that the catalytic hydrotreatment leads to enhanced quality of the gasoline, kerosine and gas oil fractions present therein.

The hydrocracking catalyst used by preference is a catalyst containing 0.1-2%w and in particular 0.2-1%w of one or more noble metals from Group VIII supported on a carrier. Preference is given to catalysts comprising platinum or palladium as Group VIII noble metal and silica-alumina as carrier. The hydrocracking in which the feed, together with added hydrogen, is passed over the noble metal catalyst is preferably carried out at a temperature of 200°-400° C. and in particular of 250°-350° C. and a pressure of 5-100 bar and in particular of 10-75 bar.

If the two-step process according to the invention is combined with a hydrocracking treatment as a third step for the preparation of middle distillates, the second and third steps can be carried out in 'series-flow', since the reaction product of the second step still contains sufficient unconverted hydrogen for carrying out the hydrocracking. It is a matter of common knowledge that carrying out a multi-step process in 'series-flow' comprises using the total reaction product—without any components being removed therefrom or added thereto—of a certain step as feed for the following step, which is carried out substantially at the same pressure as the preceding step. The separation of the steam formed in the second step and the separation of the excess hydrogen present are carried out in the third step. When the second and third steps are carried out in 'series-flow', the steam present in the reaction product of the first step is preferably separated after the first step. However, if desired the entire three-step process can be carried out in series-flow.

The invention is now illustrated with the aid of the following example.

EXAMPLE

This example relates to the preparation of $C_5^+$ hydrocarbons, starting from a natural gas substantially consisting of methane. The preparation was carried out by successively subjecting the natural gas, together with a recycle stream, in the first step to steam reforming, removing steam from the reaction product by cooling and part of the hydrogen by applying "pressure swing adsorption" using a molecular sieve, subjecting the reaction product freed of steam and part of the hydrogen in a second step to hydrocarbon synthesis, dividing the reaction product of the second step by cooling into a liquid fraction comprising the desired $C_5^+$ hydrocarbons and the water formed in the second step, and a gaseous fraction comprising $C_4^-$ hydrocarbons, carbon dioxide and uncoverted hydrogen and carbon monoxide, and recycling the gaseous fraction to the first step. Further information on the conditions used for the preparation and the results obtained is given hereinafter.

Steam reforming

The steam reforming was carried out at a temperature of 850° C. and a pressure of 22 bar and by using a steam/hydrocarbon ratio of 3.70 g mol $H_2O$/g mol $CH_4$ present in the fresh feed. The catalyst used was a $Ni/Ca/K/Al_2O_3$ composition containing 13 pbw nickel, 12 pbw calcium and 0.2 pbw potassium per 100 pbw alumina.

Hydrocarbon synthesis

The hydrocarbon synthesis was carried out at a temperature of 220° C., a pressure of 20 bar and a space velocity of $850 Nl(H_2+CO).l^{-1}.h^{-1}$ and by using a $Co/Zr/SiO_2$ catalyst which had previously been subjected to reduction at 250° C. in a hydrogen-containing gas. The catalyst, which contained 25 pbw cobalt and 0.9 pbw zirconium per 100 pbw silica, had been prepared by single-step impregnation of silica carrier with a solution of cobalt nitrate in water, followed by single-step impregnation of the cobalt-loaded carrier with a solution of zirconium nitrate in water. In both impregnation steps there was used a quantity of solution whose volume corresponded substantially with the pore volume of the carrier. After the two impregnation steps the material was dried and then calcined at 500° C. The catalysts L was 98 mg/ml and its S was 96 m²/ml and therefore L/S was 1.02 mg/m².

The synthesis gas used as feed in the second step had a $H_2/CO$ molar ratio of 2.1 and contained 24%v carbon dioxide. In the second step the synthesis gas conversion achieved was 90%. The $C_5+$ selectivity, calculated on $C_1+$ was 84%.

What is claimed is:

1. A process for the preparation of $C_5+$ hydrocarbons from $C_4-$ hydrocarbons by the process of:
   (a) steam reforming said $C_4-$ hydrocarbons in the presence of steam at a temperature of 500°-1200° C., a pressure of 2-40 bars, a steam hydrocarbon ratio of 1-10 g mol $H_2O$/g atm C and a catalyst comprising one or more metals from the iron group supported on an inorganic oxide carrier to form a synthesis feed gas of carbon monoxide and hydrogen;
   (b) synthesizing said carbon monoxide and hydrogen into said $C_5+$ hydrocarbons by contact of said carbon monoxide and hydrogen at a temperature of 125° to 350° C. and a pressure of from 5 to 100 bar in the presence of a synthesis catalyst consisting essentially of from 3 to 60 pbw cobalt and 0.1-100 pbw of at least one metal chosen from the group consisting of zirconium, titanium and chromium per 100 pbw of a silica, alumina or a silica/aluminum carrier in accordance with the formula:

$$(3+4R) > (L/S) > (0.3+0.4R)$$

where
   L = the total quantity of cobalt present on the catalyst, expressed as mg Co/ml catalyst,
   S = the surface area of the catalyst expressed as m²/ml catalyst and,
   R = the weight ratio of the quantity of cobalt deposited on the catalyst by kneading to the total quantity of cobalt present on the catalyst to produce a synthesis gas product stream comprising said $C_5+$ hydrocarbons, water, hydrogen, carbon monoxide, carbon dioxide and $C_4-$ hydrocarbons;
   (c) separating said synthesis product gas into a separate liquid phase comprising $C_5+$ hydrocarbons and water and into a separate gaseous phase comprising carbon monoxide, carbon dioxide, hydrogen and $C_4-$ hydrocarbons;
   (d) separating at least a portion of said hydrogen from said carbon monoxide, carbon dioxide and $C_4-$ hydrocarbons from said gaseous phase; and
   (e) recycling at least a portion of said gaseous phase after hydrogen separation in step (d) to said steam reforming of step (a).

2. The process as claimed in claim 1, characterized in that it said $C_4-$ hydrocarbons as the feed to said steam reforming consist substantially of methane.

3. The process as claimed in claim 1, characterized in that said feed to said steam reforming is natural gas.

4. The process as claimed in claim 1, characterized in that said steam reforming is carried out at a temperature of 700°-1000° C., a pressure of 2-25 bar and a steam/hydrocarbon ratio of 1.5-5 g mol $H_2O$/g atom C and in the presence of a nickel-containing catalyst.

5. The process as claimed in claim 1, characterized in that said synthesis catalyst contains per 100 pbw carrier 15-50 pbw cobalt and either 0.1-5 pbw of the metal selected from group consisting of zirconium, titanium and chromium if during the synthesis catalyst's preparation cobalt is deposited first and the metal selected from group consisting of zirconium, titanium and chromium is deposited second, or 5-40 pbw of the metal selected from group consisting of zirconium, titanium and chromium if, in the preparation, the metal selected from group consisting of zirconium, titanium and chromium is deposited first and cobalt deposited second.

6. The process as claimed in claim 5, characterized in that said catalyst comprises zirconium and silica is chosen as said carrier.

7. The process as claimed in claim 1, characterized in that said synthesis of said $C_5+$ hydrocarbon is carried out at a temperature of 175°-275° C. and a pressure of 10-75 bar.

8. The process as claimed in claim 7, characterized in that said hydrogen derived from said synthesis reaction product in said separated gaseous phase is carried out by membrane separation or by pressure swing adsorption.

9. The process as claimed in claim 8, characterized in that steam is removed from the steam reforming reaction product of carbon monoxide and hydrogen and that hydrogen is removed from the gaseous fraction obtained after said synthesis of carbon monoxide and hydrogen to from said $C_5+$ hdrocarbons.

10. The process as claimed in claim 9, characterized in that steam is removed from said steam reforming reaction product of carbon monoxide and hydrogen and from said gaseous phase after gas/liquid separation in step (d) and that part of the hydrogen is removed from the steam reforming reaction product of carbon monoxide and hydrogen and is removed from the gaseous fraction obtained after the separation of the gas/liquid phase in step (d).

11. The process of claim 1 further characterized in that a portion of the separated liquid phase obtained in step (d) has an initial boiling point above the final boiling point of the heaviest middle distillate desired as said $C_5+$ hydrocarbons, and said portion is subjected to hydrocracking by contacting said portion at elevated temperature and pressure with a catalyst comprising one or more noble metals from Group VIII supported on a carrier.

12. The process as claimed in claim 11, characterized in that said hydrocracking is performed in the presence of a catalyst containing 0.2-1%w of one or more noble metals from Group VIII.

13. The process as claimed in claim 12, characterized in that said hydrocracking is performed in the presence of a catalyst containing 0.2-1%w of one or more noble metals from Group VIII.

14. The process as claimed in claim 13, characterized in that said hydrocracking is performed in the presence of a catalyst containing platinum or palladium as said noble metal from Group VIII and silica-alumina as a carrier.

15. The process as claimed in claim 14, characterized in that said hydrocracking is carried out at a temperature of 200°-400° C. and a pressure of 5-100 bar.

16. The process as claimed in claim 15, characterized in that said hydrocracking is carried out at a temperature of 250°-350° C. and a pressure of 10-75 bar.

* * * * *